(12) United States Patent
Fei (10) Patent No.: US 10,959,649 B2
(45) Date of Patent: Mar. 30, 2021

(54) SYSTEMS AND METHODS FOR STRIDE LENGTH CALIBRATION

(71) Applicant: Beijing Shunyuan Kaihua Technology Limited, Beijing (CN)

(72) Inventor: Ming Shun Fei, Coquitlam (CA)

(73) Assignee: BEIJING SHUNYUAN KAIHUA TECHNOLOGY LIMITED, Beijing (CN)

( * ) Notice: Subject to any disclaimer, the term of this patent is extended or adjusted under 35 U.S.C. 154(b) by 197 days.

(21) Appl. No.: 14/608,571

(22) Filed: Jan. 29, 2015

(65) Prior Publication Data

US 2015/0141873 A1 May 21, 2015

(51) Int. Cl.
*A61B 5/11* (2006.01)
*A61B 5/00* (2006.01)
*G01C 22/00* (2006.01)
*A61B 5/0205* (2006.01)

(52) U.S. Cl.
CPC ............. *A61B 5/112* (2013.01); *A61B 5/1118* (2013.01); *A61B 5/681* (2013.01); *G01C 22/006* (2013.01); *A61B 5/0205* (2013.01); *A61B 5/1123* (2013.01); *A61B 5/742* (2013.01)

(58) Field of Classification Search
CPC ..... A61B 5/112; A61B 5/1118; A61B 5/1123; A61B 5/681; G01C 22/006
See application file for complete search history.

(56) References Cited

U.S. PATENT DOCUMENTS

| | | | | |
|---|---|---|---|---|
| 6,546,336 B1* | 4/2003 | Matsuoka | ............ | G01C 22/006 701/408 |
| 7,647,196 B2* | 1/2010 | Kahn | ................... | A61B 5/0022 702/142 |
| 8,460,001 B1* | 6/2013 | Chuang | .............. | G09B 19/0038 434/247 |
| 2001/0022828 A1* | 9/2001 | Pyles | ................... | G01C 22/006 377/24.2 |
| 2010/0250179 A1* | 9/2010 | Mariano | ............... | G01C 21/165 702/96 |
| 2011/0003665 A1* | 1/2011 | Burton | .................... | G04F 10/00 482/9 |
| 2013/0190657 A1* | 7/2013 | Flaction | ............... | A61B 5/1038 600/595 |

(Continued)

*Primary Examiner* — Devin B Henson
(74) *Attorney, Agent, or Firm* — Young Basile Hanlon & MacFarlane, P.C.

(57) ABSTRACT

Described herein are systems, devices, and methods for determining a user's stride length and monitoring various aspects of the user's activities. An apparatus worn or carried by the user may determine and track when a user takes a step and, based at least in part on user-specific information, determine an estimated stride length of the user associated with a respective step rate or step rate range. The apparatus may further monitor the physical location, speed, or pace of the user during an activity and, in conjunction with step count information, determine a verified stride length for the user associated with a respective step rate or step rate range. The estimated and verified stride length determinations may be stored and used to determine one or more aspects of a user's subsequent activities, including but not limited to pace, speed, and calorie expenditure information, even when physical location information is unavailable.

20 Claims, 5 Drawing Sheets

(56) References Cited

U.S. PATENT DOCUMENTS

| | | | |
|---|---|---|---|
| 2013/0197857 A1* | 8/2013 | Lu | G01S 19/19 |
| | | | 702/141 |
| 2014/0129177 A1* | 5/2014 | Gyorfi | G01C 25/005 |
| | | | 702/160 |
| 2014/0330141 A1* | 11/2014 | Banet | A61B 5/0205 |
| | | | 600/484 |
| 2015/0285659 A1* | 10/2015 | Curtis | G01C 25/005 |
| | | | 702/97 |

* cited by examiner

User Profile

| sex | height (m) | weight (kg) | date of birth | inseam (m) | SBL (m/step) |
|---|---|---|---|---|---|
| M/F | A | B | DD/MM/YYYY | C | D |

412 — sex
414 — height (m)
416 — weight (kg)
418 — date of birth
420 — inseam (m)
422 — SBL (m/step)
410 — User Profile

| Step Rate (steps/min) | Estimated Stride Length (m/step) | Verified Stride Length (m/step) | Speed (m/min) | Pace (min/m) |
|---|---|---|---|---|
| SR < 80 | $SL_{EST1} = BSL*a$ | $SL_{V1} = ---$ | $SR*SL_1$ | $(1/SR)*(1/SL_1)$ |
| 80 ≤ SR < 90 | $SL_{EST2} = BSL*b$ | $SL_{V2} = ---$ | $SR*SL_2$ | $(1/SR)*(1/SL_2)$ |
| 90 ≤ SR < 120 | $SL_{EST3} = BSL*c$ | $SL_{V3} = 0.791$ | $SR*SL_{V3}$ | $(1/SR)*(1/SL_3)$ |
| 120 ≤ SR < 140 | $SL_{EST4} = BSL*d$ | $SL_{V4} = ---$ | $SR*SL_4$ | $(1/SR)*(1/SL_4)$ |
| 140 ≤ SR < 160 | $SL_{EST5} = BSL*e$ | $SL_{V5} = 1.064$ | $SR*SL_{V5}$ | $(1/SR)*(1/SL_5)$ |
| 160 ≤ SR < 180 | $SL_{EST6} = BSL*f$ | $SL_{V6} = 1.095$ | $SR*SL_{V6}$ | $(1/SR)*(1/SL_6)$ |
| SR ≥ 180 | $SL_{EST7} = BSL*g$ | $SL_{V7} = ---$ | $SR*SL_7$ | $(1/SR)*(1/SL_7)$ |

Fig. 4

SYSTEMS AND METHODS FOR STRIDE LENGTH CALIBRATION

FIELD OF THE DISCLOSURE

The embodiments relate generally to systems and methods that use data collected by a wearable device to calculate, among other things, the stride length, pace, and speed of a user and, more specifically, systems and methods for determining a user's stride length based, in part, on user information, historical data, and/or a step count.

BACKGROUND

Many portable and/or wearable devices have been developed for determining when a user takes a step during a fitness training session or other daily activity. Such devices and systems are now commonly found in so-called "activity trackers" and "health monitors." These devices typically comprise an accelerometer, e.g., a three-axis accelerometer, and software for interpreting raw data gathered by the accelerometer. The software may determine when a user has taken a step based on patterns identified in the accelerometer data, acceleration magnitudes that exceed predetermined thresholds, peak-to-peak threshold crossings in the data, dominant frequencies in the data, and/or a number of other known methods.

The step counting data can then be used in various applications, including but not limited to, recording the number of steps taken by the user during a monitored period (e.g., hourly, daily, weekly, etc.), estimating a number of calories burned by the user during the monitored period, and/or characterizing an activity level achieved by the user during the monitored period.

Step counting data can also be interpreted in conjunction with GPS tracking data collected by the portable or wearable device in order to calculate a stride length of the user. For example, a wearable device may determine that a user has taken a number of steps during the monitored period and traveled some distance. The user's stride length (SL) can then be calculated by dividing the distance traveled by the number of steps taken. Other information regarding the user's activity can also be determined using the GPS tracking data in conjunction with time, such as the user's pace (time/distance) and speed (distance/time).

Stride length, pace, and speed information become more difficult to calculate, however, when no GPS data is available, such as when no GPS signal can be received or when a user's position isn't changing (e.g., the user is running or walking on a treadmill). Accurate calculation of stride length may be further complicated based on the variance of a user's stride length at different paces or speeds. For example, a user's stride length may be shorter when running or walking at a first pace/speed than when the user is running or walking at a second, faster pace/speed.

Thus, a need exists for improved systems, devices, and techniques for determining, among other things, a user's stride length, pace, and speed, particularly when GPS information is limited or unavailable. Moreover, improved systems, devices, and techniques are needed to ensure the accuracy, reliability, and durability of such information.

SUMMARY OF THE DISCLOSURE

In accordance with certain embodiments of the present disclosure, components and processes suited for use in physiological monitoring devices that are used for physical training, exercise, activity, and/or general wellness monitoring are disclosed. In some embodiments, the monitoring devices may be a wrist watch, bracelet, or arm band comprising one or more components. The monitoring devices may comprise one or more accelerometers, including but not limited to a three-axis accelerometer. In such embodiments, acceleration data collected by the accelerometer may be used to determine when and at what frequency a user takes a step. The monitoring devices may further comprise other components for tracking the user's physical location (e.g., a GPS module), a time keeping component (e.g., a clock, stopwatch, and/or timer), one or more communication modules. The data from one or more such components may be used in conjunction with data collected by the accelerometer(s) to make further determinations and/or inferences regarding the user's activity level, wellness, or physiological state.

In one embodiment, monitoring devices described herein may monitor a user's step rate (i.e., steps/minute) by counting the number of steps taken by a user in a predetermined time frame (e.g., 10 seconds, 30 second, 1 minute, 30 minutes, etc.). Based on the user's step rate, an estimated stride length may be calculated. In further embodiments, a user's estimated stride length may be further based on other user-specific information in conjunction with the user's step rate. For example, the user's sex, height, weight, age, inseam, outseam, and/or other user-specific information may be considered in conjunction with the user's step rate to determine an estimated stride length. In other embodiments, activity-specific information may be used in conjunction with the user's step rate to determine an estimated stride length. In such embodiments, the user may provide information regarding his or her ongoing or anticipated activity to the monitoring device. For example, the user may input activity-specific information to the monitoring device indicating that the user is beginning a run, a workout, or a walk. Additionally or alternatively, information collected by the monitoring device's accelerometer(s) and/or other components may be analyzed to determine an activity type that the user is currently or may plan to engage in. For instance, larger amplitudes in acceleration data may be indicative of a user engaging in strenuous activity such as a run or intense workout, whereas relatively smaller amplitudes in acceleration data may be indicative of a less strenuous activity such as walking.

In one aspect, the monitoring devices may comprise a database or records correlating a user's step rate with a stride length. For example, where the monitoring device determines a user's step rate to be within a first range, the database may associate that first range with an estimated stride length. Similarly, where the monitoring device determines the user's step rate to be within a second range, the database may be used to associate that second range with another estimated stride length different from the first estimated stride length. In further embodiments, relatively high step rates may be associated with longer stride lengths and relatively low step rates may be associated with shorter stride lengths.

In another aspect, the monitoring device described herein may comprise a GPS module for collecting information regarding the user's physical location. Alternatively, the monitoring device may be in communication with another device having GPS capability and/or some other mechanism for collecting information regarding the user's physical location.

In some embodiments, location information pertaining to the user may be used in conjunction with a determined step rate in order to determine a verified stride length. For example, the monitoring device may determine that a user has taken 2,000 steps and traveled approximately one mile (i.e., 5,280 feet). Thus, the monitoring device can determine that the user's average stride length during the 2,000 steps was 2.64 feet.

In a further aspect, verified stride length information may be associated with the user's measured step rate during the same interval and recorded by the monitoring device. In some embodiments, the verified stride length information associated with a particular step rate or range of step rate may be substituted for the estimated stride lengths discussed above. In further embodiments, the verified stride length associated with a first step rate or range of step rate may be used to inform the estimated stride length associated with other step rates or ranges of step rates. For example, where the verified stride length associated with a first step rate or range of step rate is longer than the estimated stride length associated with the first step rate or range of step rate, then it may be inferred that the stride length of the user at other step rates or ranges of step rates is longer than the estimated stride lengths associated with those other step rates or ranges of step rates.

The database records, including estimated and verified stride lengths associated with respective step rates and/or ranges of step rates may be accessed by the monitoring device during future activities. For example, when the user is engaged in an activity during which GPS data is unavailable (such as, but not limited to, when the user is on a treadmill, walking a limited distance, running wind sprints, jogging around a tracking, or engaging in an activity at a location where a GPS signal is unavailable), the apparatus may determine a user's step rate, associate that step rate with a historical or stored estimated or verified stride length, and based at least in part on that information, determine the user's current stride length, pace (time/distance), and/or speed (distance/time).

Additional objects and advantages of the present disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are illustrative and explanatory only and are not restrictive of the claims.

The accompanying drawings, which are incorporated in and constitute a part of this specification, illustrate several embodiments and together with the description, serve to explain the principles of the disclosure.

DESCRIPTION OF THE EMBODIMENTS

Disclosed herein are embodiments of an apparatus for use in activity monitoring, physical training, athletic activity, physical rehabilitation, exercise, patient monitoring, and/or general wellness monitoring. Of course, these examples are only illustrative of the possibilities and the device described herein may be used in any suitable context.

In one aspect, the apparatus may comprise one or more accelerometers incorporated into a portable or wearable device. In other embodiments, rather than comprising one or more accelerometers, the portable or wearable device may communicate with another device or system comprising one or more accelerometers. The accelerometers may be of any suitable type for detecting a step taken by a user carrying or wearing the device. In one embodiment, the device may comprise a three-axis accelerometer. In other embodiments, the device may comprise a single-axis accelerometer, a two-axis accelerometer, or some other suitable accelerometer.

In another aspect, the apparatus may receive acceleration data from the one or more accelerometers and, based at least in part on the acceleration data, determine and/or record if or when a user carrying or wearing the device takes a step. In further embodiments, the apparatus may comprise (or be in communication with) a time keeping component. In such embodiments, the apparatus may further determine and/or record the user's step rate (i.e., a number of steps per time interval).

In a further aspect, the apparatus may comprise or be in communication with a database containing one or more records associating step rates (or ranges of step rates) with an estimated stride length for the user. The estimated stride length may be based, at least in part, on the step rate. In further embodiments, the estimated stride length may be based, at least in part, on other user-specific information, such as the user's sex, height, weight, age, inseam, outseam, and/or other attributes. The estimated stride length may also be based, at least in part, on an activity in which the user may be engaged, such as walking, running, jogging, or sprinting.

In another aspect, the apparatus may comprise or be in communication with a GPS module configured to collect and/or transmit data associated with the user's physical location. In some embodiments, data received from the GPS module may be used in conjunction with the step rate information to determine a verified stride length. In such embodiments, the aforementioned database may be updated to include verified stride length data associated with a step rate or range of step rates. In further embodiments, the verified stride length data associated with a first step rate or range of step rates may be used to calibrate or improve the estimated stride lengths associated with other step rates or ranges of step rates.

In a further aspect, the database records, including estimated and verified stride lengths associated with respective step rates and/or ranges of step rates may be accessed by the apparatus at a later time. For example, when the user is engaged in an activity, exercise, or training session where GPS data is unavailable (such as when the user is on a treadmill, running around a tracking, or engaging in an activity at a location where a GPS signal is unavailable, the apparatus may determine a user's step rate, associate that step rate with a historical or stored estimated or verified stride length, and based at least in part on that information, determine the user's current stride length, pace (time/distance), and/or speed (distance/time).

While the systems and devices described herein may be depicted as wrist worn devices, one skilled in the art will appreciate that the systems, devices, and methods described below can be implemented in other contexts, including the sensing, measuring, and recording of data gathered from a device worn at any suitable portion of a user's body, including but not limited to, other portions of the arm, other extremities, the head, and/or the chest. In other embodiments, rather than a wearable device, the device may be carried by the user or on the user's person (e.g., in a purse, backpack, etc.).

Reference will now be made in detail to certain illustrative embodiments, examples of which are illustrated in the accompanying drawings. Wherever possible, the same reference numbers will be used throughout the drawings to refer to the same or like items.

Figure 1:
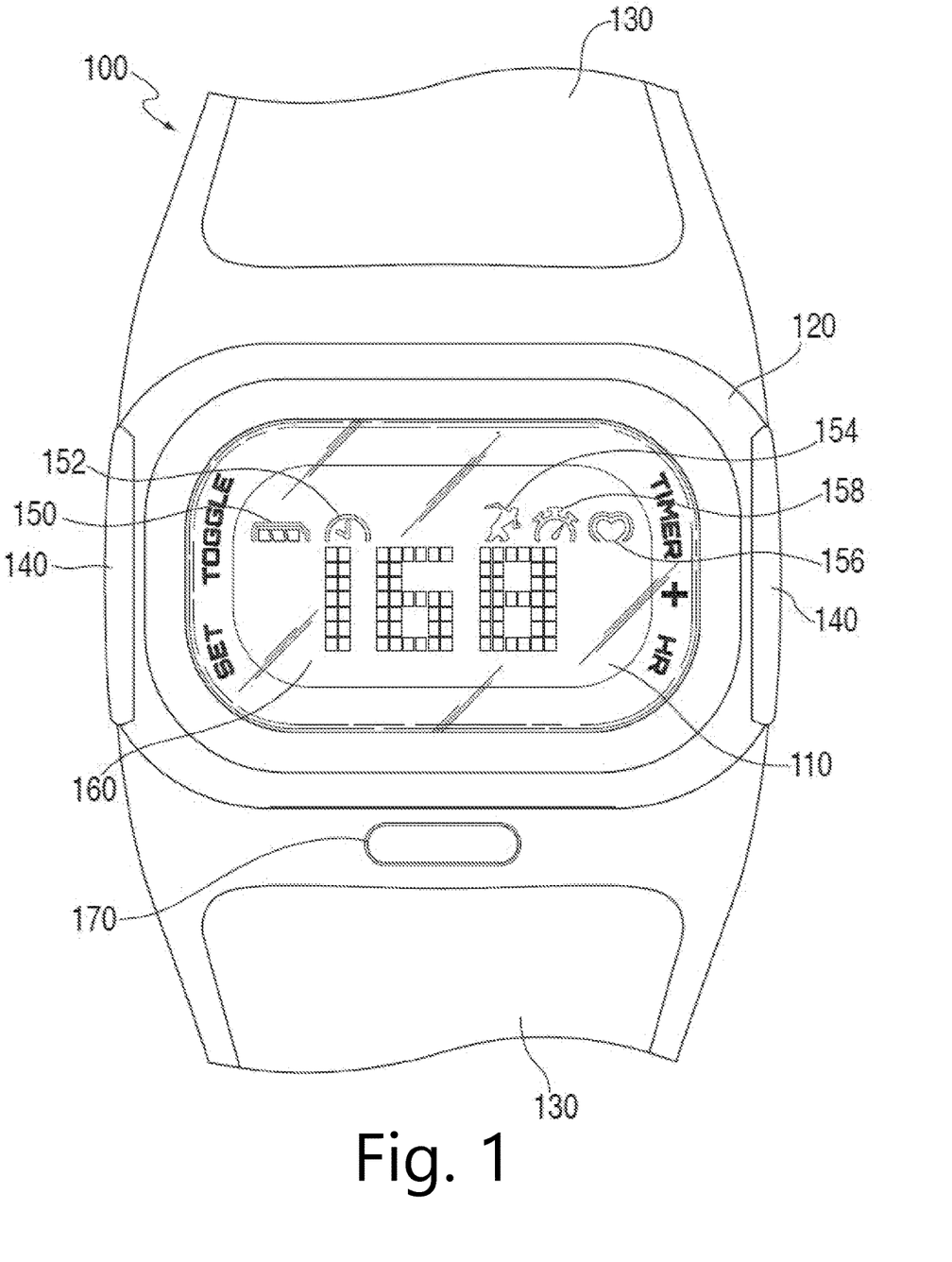
FIG. 1 depicts some aspects of an illustrative embodiment of an apparatus as described herein.

FIG. 1 depicts an illustrative embodiment of an apparatus 100. In one aspect, apparatus 100 may be a device carried or worn by a user to sense, collect, monitor, and/or display information pertaining to the user's activity and/or one or more physiological parameters. In the depicted embodiment, apparatus 100 may comprise a wrist watch. In alternative embodiments, apparatus 100 may be a bracelet or an arm band. In further embodiments, apparatus 100 may be any wearable monitor device configured for positioning at a user's wrist, arm, another extremity of the user, or some other area of the user's body. In still further embodiments, apparatus 100 may be a portable device carried by the user, clipped to the clothing of the user, or carried on the user's person (e.g., inside a pocket, purse, backpack, etc.).

In another aspect, apparatus 100 may comprise one or more accelerometers (not depicted) and components for processing and displaying information that may or may not be related to a user's past or present activity, activity level, physical training sessions, or general wellness and/or one or more physiological parameters of a user. For example, in one embodiment, apparatus 100 may sense, process, and/or display the time, a timer or stopwatch, a distance traveled, a pace, a speed, calories burned, steps taken, step rate, an activity level, heart rate information, and/or other user- or activity-specific information. In a further aspect, apparatus 100 may house a display unit 110 for displaying or otherwise conveying information to the user. In one embodiment, display unit 110 may comprise a dot matrix liquid crystal display. In alternative embodiments, display unit 110 may comprise some other suitable display.

In a further aspect, apparatus 100 may comprise a casing 120 and one or more bands 130 extending from opposite edges of casing 120 for securing apparatus 100 to the user. In one embodiment, band(s) 130 may comprise an elastomeric material. In alternative embodiments, band(s) 130 may comprise some other suitable material, including but not limited to, a fabric or metal material.

Apparatus 100 may further comprise one or more switches 140 operable for accepting input from the user. Switches 140 may comprise any suitable device for accepting input from the user including, but not limited to, a switch, button, touchscreen, or sensor. FIG. 1 depicts a pair of opposing switches 140, one positioned on either side of casing 120. Other embodiments, however, may comprise fewer or additional switches. Moreover, the switches may be located at any suitable location on apparatus 100.

In further embodiments, switches 140 may be incorporated into display unit 110. For example, switches 140 may comprise "soft" buttons configured to accept input from the user via a touchscreen.

In another aspect, the user may manipulate switches 140 for setting the time display, establishing the operational mode of the heart rate monitor, and/or otherwise configuring/interacting with apparatus 100 during use.

Casing 120 may further comprise switch indicators for providing the user information regarding each switch. In one embodiment, casing 120 may comprise words and/or symbols such as "set," "toggle," "timer," "+," and "HR" corresponding to the switches and providing the user with an indication of a function that may be achieved by manipulation of the respective switch. Of course, the switch indicators depicted in FIG. 1 are only illustrative of the possibilities. Casing 120 may comprise no, fewer, additional, or alternative indicators.

Display unit 110 may further comprise one or more small icons for conveying information to the user. In one embodiment, the one or more icons may be located in an upper portion of display 110 to indicate operational and/or conditional aspects of apparatus 100. For example, an icon 150 may be illuminated whenever the watch is energized to indicate battery condition; an icon 152 may be illuminated when display 110 indicates the time of day; an icon 154 and 156 may be illuminated when apparatus 100 is operating in the exercise mode and/or the user's heart rate is being displayed; and an icon 158 may be illuminated when apparatus 100 is operating in the exercise mode and the exercise duration is being recorded. Additionally, featured information (e.g., a speed, pace, or heart rate, to name a few) may be displayed in a central region 160 of display 110 in the same display region displaying time when used as a conventional watch. Of course, the aforementioned examples of icons 150-160, each icon's function, depicted appearance, and/or respective position within display unit 110 are only illustrative of the possibilities. Fewer, additional, or alternative icons and/or icon locations are also possible.

Apparatus 100 may also comprise a communication status indicator 170. Status indicator 170 may comprise an outward facing light source viewable by the user when the watch is in use. In one aspect, the light source may comprise one or more lights, such as LEDs. In one embodiment, the light source may comprise a plurality of LEDs, each of a different color. In this manner, the color of the LED illuminated may convey additional information to a user regarding the communication status of apparatus 100. In another aspect, when apparatus 100 is in communication with another device via a suitable communication channel, such as Bluetooth communication, status indicator 170 may illuminate light of a first color. Where apparatus 100 is in communication with another device via some alternative communication channel, status indicator 170 may illuminate light of a second color. Alternatively, or additionally, status indicator 170 may illuminate light of another color when ongoing communication with another device is terminated and/or apparatus 100 ends or initiates an operational state. Again, these examples are only illustrative of the possibilities and status indicator 170 may illuminate one or more light sources corresponding to one or more colors to indicate or convey any suitable information to the user, including but not limited to, one or more notifications that may be conveyed during an activity or during monitoring. For example, where apparatus 100 may be configured to monitor the user's heart rate, indicator 170 may illuminate light of a first color when the user's heart rate is in a first numerical range, illuminate light of a second color when the user's heart rate is in a second numerical range, and illuminate light of a third color when the user's heart rate is in a third numerical range. Similarly, where apparatus 100 may be configured to monitor the user's pace, indicator 170 may illuminate light of a first color when the user's pace is in a first numerical range or below a predetermined range, illuminate light of a second color when the user's pace is within a second numerical range or within a predetermined range, and illuminate light of a third color when the user's pace is in a third numerical range or above a predetermined range. In this manner, a user may be able to detect activity or physiological information at a glance or through his or her peripheral vision. This may be particularly useful in instances when alphanumeric information is not displayed at display unit 110 and/or alphanumeric information may be difficult to read in the context of the activity (e g, running, sprinting, climbing, etc.).

It should be noted that although a wrist watch-like embodiment of apparatus 100 is depicted in FIG. 1, apparatus 100 may comprise alternative wearable embodiments such as bands, bracelets, straps, or clips. Such embodiments may include some or all of the features of the watch embodiment described above. For example, some embodiments may not comprise a display unit 110 or a casing 120. Rather, the various components of apparatus 100 may be housed or embedded in a single strap 130. In such embodiments, information may be conveyed to a user using tactile feedback (e.g., vibration), sound (e.g., tones of varying volume, pitch, frequency, and duration), and light (e.g., LEDs of one or more colors that may blink or be illuminated for some predetermined period).

In still further embodiments, apparatus 100 may not comprise a wearable device. Rather, apparatus 100 may be a device configured for carrying by the user or carried on the user's person. For example, apparatus 100 may be configured for placing in the user's pocket, purse, backpack, or shoe. Such embodiments may include some or all of the features of the watch embodiment described above.

In another aspect, apparatus 100 may be configured to communicate information to a user via a secondary device such as a smart phone, tablet, or personal computer. In such embodiments, information collected, analyzed, or stored at apparatus 100 may be communicated to a secondary device for further analysis, storage, or presentation to the user. Conversely, apparatus 100 may be configured to receive information from such secondary devices for further analysis, storage, or presentation to the user.

Figure 2:
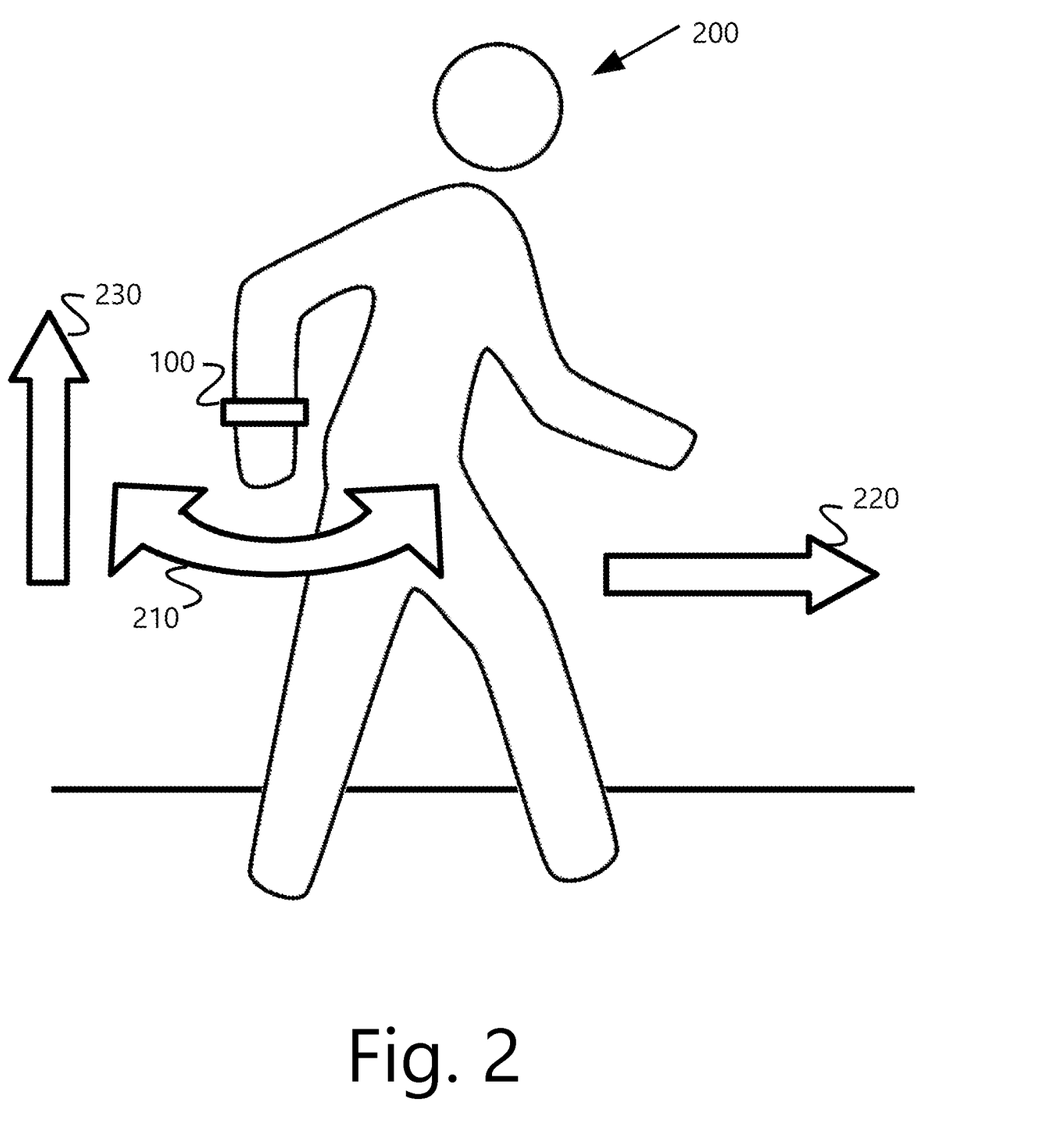
FIG. 2 depicts some aspects of an illustrative embodiment of an apparatus as described herein.

FIG. 2 depicts an illustrative embodiment of apparatus 100 in use. In one aspect, user 200 may carry or wear apparatus 100 during an activity. In the embodiment depicted in FIG. 2, apparatus 100 is a wrist-worn device. In other embodiments, apparatus 100 may be carried or worn by the user in any suitable manner, including but not limited to, those described herein.

In one aspect, apparatus 100 may comprise one or more accelerometers (not depicted), including but not limited to, a three-axis accelerometer. Generally, one or more accelerometers may be configured to convert the movement or acceleration of a body into digital measurements. The acceleration data collected or transmitted by the accelerometer(s) may comprise information regarding the frequency, duration, intensity, and patterns of movement associated with the body, all or some of which may be used to determine when a user has taken a step and/or an activity type that the user may be engaged in. For example, in some embodiments, patterns associated with a user walking or running may be identified and movements exceeding predetermined amplitude thresholds may be counted as a step. A frequency associated with such threshold-exceeding amplitudes may be used, for example, to determine whether the user is walking or running. In further embodiments, moving averages of such data may be used to further refine a step count and/or take potential uneven steps or missteps into account. In other embodiments, other systems, devices, or methods may be used to determine when a user takes a step and/or refine initial determinations.

In another aspect, the use of a three-axis accelerometer may improve the accuracy of step determinations by taking other environmental considerations into account, including but not limited to, lateral movements of a user, elevation and/or terrain changes, and the swinging or rhythmic movement of one or more body portions or appendages (depending on where or how apparatus 100 is worn or carried).

As shown in FIG. 2, the accelerometer may collect acceleration data attributable to the swinging or rhythmic movement 210 specific to a body portion or appendage associated with apparatus 100 (e.g., the swinging motion of an arm during running or walking), the user's forward or backward movement 220 resulting from a step, and/or the user's upward or downward movement 230 resulting from or following a step, respectively.

In use, acceleration data attributable to swinging/rhythmic movement 210 that masks or interferes with acceleration data attributable to movements 220 and 230 may be accounted for so as to arrive at accurate step determinations. Further details regarding the interpretation of acceleration data and/or determining when a user takes a step are beyond the scope of this disclosure as several such systems, devices, and methods are known. Suffice it to say, apparatus 100 may apply one or more filters or pattern recognition methods (embodied as either hardware or software components) to acceleration data received from the one or more accelerometers, depending on where apparatus 100 is worn or carried by the user (e.g., a wrist-worn device, an upper arm band, a belt-clipped device, a shoe-based device, or a device carried in a backpack or purse, etc.) and/or the type of activity the user is engaged in (e.g., jogging, running, cross-training, weightlifting, etc.). Such filters or pattern recognition methods may be configured to filter or remove "noise" from the acceleration data that may be attributable to accelerations unrelated to the user's steps.

In addition to information received from the one or more accelerometers of apparatus 100, other information collected or detected at apparatus 100 may be used to determine when and with what frequency a step is taken. For example, acceleration information may be interpreted in light of GPS data, activity-specific information, and/or information input by a user to determine when a step is taken by the user. Alternatively, such information may be used to confirm the accuracy of acceleration data-based step counts. Of course, in other embodiments, additional or alternative information may be considered when determining the occurrence of a step or confirming the occurrence of a step.

Figure 3:
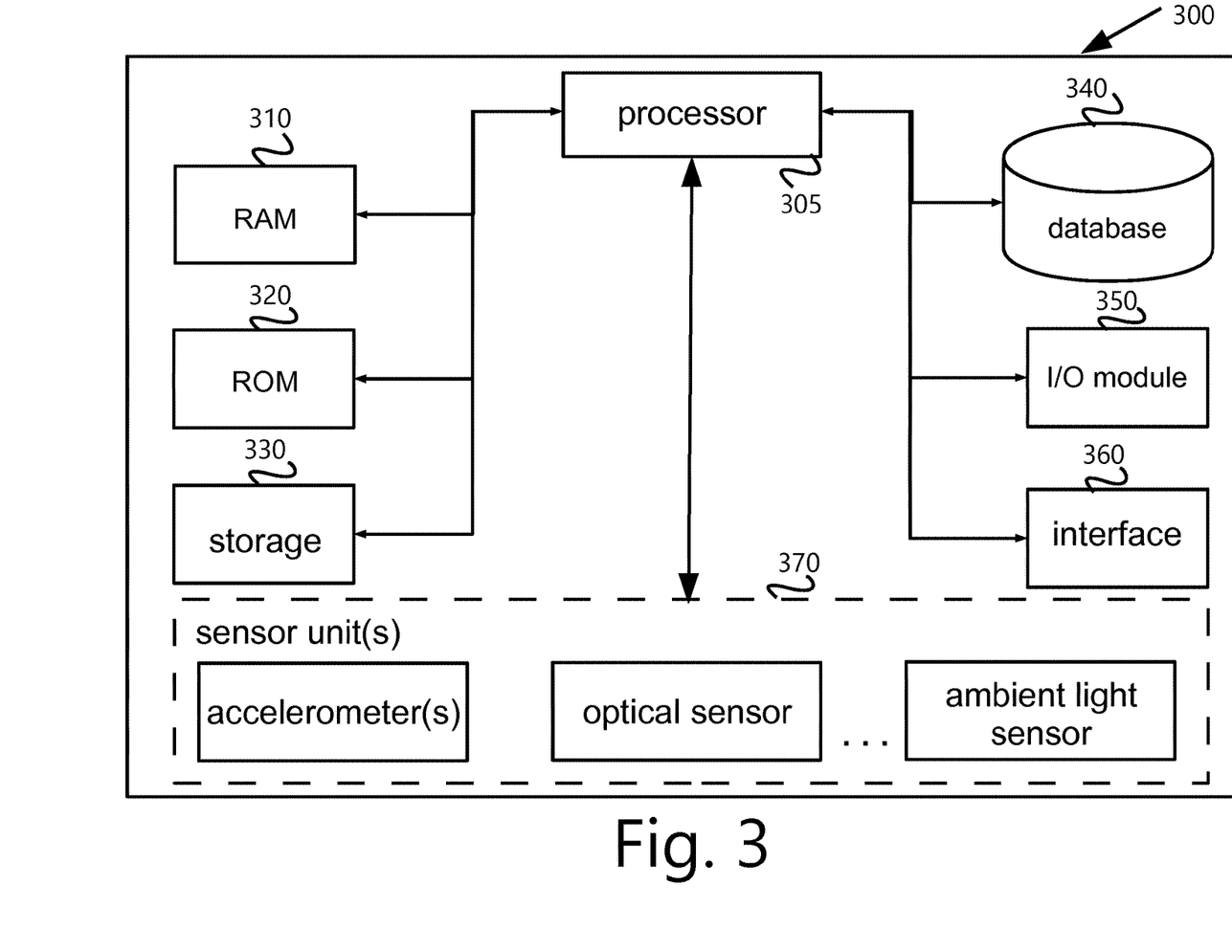
FIG. 3 depicts some aspects of an illustrative embodiment of a computing system as described herein.

FIG. 3 depicts an illustrative processor-based computing system 300 representative of the type of computing system that may be present in or used in conjunction with any aspect of apparatus 100 comprising electronic circuitry. For example, processor-based computing system 300 may be used in conjunction with any one or more of transmitting signals to and from the one or more accelerometers, sensing or detecting signals received by one or more sensors of apparatus 100, processing received signals from one or more components or modules of apparatus 100 or a secondary device, and storing, transmitting, or displaying information. Computing system 300 is illustrative only and does not exclude the possibility of another processor- or controller-based system being used in or with any of the aforementioned aspects of apparatus 100.

In one aspect, system 300 may include one or more hardware and/or software components configured to execute software programs, such as software for storing, processing, and analyzing data. For example, system 300 may include one or more hardware components such as, for example, processor 305, a random access memory (RAM) module 310, a read-only memory (ROM) module 320, a storage system 330, a database 340, one or more input/output (I/O) modules 350, an interface module 360, and one or more sensor modules 370. Alternatively and/or additionally, system 300 may include one or more software components such as, for example, a computer-readable medium including computer-executable instructions for performing methods consistent with certain disclosed embodiments. It is contemplated that one or more of the hardware components listed above may be implemented using software. For example, storage 330 may include a software partition associated with one or more other hardware components of system 300. System 300 may include additional, fewer, and/or different components than those listed above. It is understood that the components listed above are illustrative only and not intended to be limiting or exclude suitable alternatives or additional components.

Processor 305 may include one or more processors, each configured to execute instructions and process data to perform one or more functions associated with system 300. The term "processor," as generally used herein, refers to any logic processing unit, such as one or more central processing units (CPUs), digital signal processors (DSPs), application specific integrated circuits (ASICs), field programmable gate arrays (FPGAs), and similar devices. As illustrated in FIG. 3, processor 305 may be communicatively coupled to RAM 310, ROM 320, storage 330, database 340, I/O module 350, interface module 360, and one more sensor modules 370. Processor 305 may be configured to execute sequences of computer program instructions to perform various processes, which will be described in detail below. The computer program instructions may be loaded into RAM for execution by processor 305.

RAM 310 and ROM 320 may each include one or more devices for storing information associated with an operation of system 300 and/or processor 305. For example, ROM 320 may include a memory device configured to access and store information associated with system 300, including information for identifying, initializing, and monitoring the operation of one or more components and subsystems of system 300. RAM 310 may include a memory device for storing data associated with one or more operations of processor 305. For example, ROM 320 may load instructions into RAM 310 for execution by processor 305.

Storage 330 may include any type of storage device configured to store information that processor 305 may need to perform processes consistent with the disclosed embodiments.

Database 340 may include one or more software and/or hardware components that cooperate to store, organize, sort, filter, and/or arrange data used by system 300 and/or processor 305. For example, database 340 may include user profile information, historical activity and user-specific information, physiological parameter information, predetermined menu/display options, and other user preferences. Alternatively, database 340 may store additional and/or different information.

I/O module 350 may include one or more components configured to communicate information with a user associated with system 300. For example, I/O module 350 may comprise one or more buttons, switches, or touchscreens to allow a user to input parameters associated with system 300. I/O module 350 may also include a display including a graphical user interface (GUI) and/or one or more light sources for outputting information to the user. I/O module 350 may also include one or more communication channels for connecting system 300 to one or more secondary or peripheral devices such as, for example, a desktop computer, a laptop, a tablet, a smart phone, a flash drive, or a printer, to allow a user to input data to or output data from system 300.

Interface 360 may include one or more components configured to transmit and receive data via a communication network, such as the Internet, a local area network, a workstation peer-to-peer network, a direct link network, a wireless network, or any other suitable communication channel. For example, interface 360 may include one or more modulators, demodulators, multiplexers, demultiplexers, network communication devices, wireless devices, antennas, modems, and any other type of device configured to enable data communication via a communication network.

System 300 may further comprise one or more sensor modules 370. In one embodiment, sensor modules 370 may comprise one or more of an accelerometer module, an optical sensor module, and/or an ambient light sensor module. Of course, these sensors are only illustrative of a few possibilities and sensor modules 370 may comprise alternative or additional sensor modules suitable for use in apparatus 100. It should be noted that although one or more sensor modules are described collectively as sensor modules 370, any one or more sensors or sensor modules within apparatus 100 may operate independently of any one or more other sensors or sensor modules. Moreover, in addition to collecting, transmitting, and receiving signals or information to and from sensor modules 370 at processor 305, any one or more sensors of sensor module 370 may be configured to collect, transmit, or receive signals or information to and from other components or modules of system 300, including but not limited to database 340, I/O module 350, or interface 360.

Figure 4:
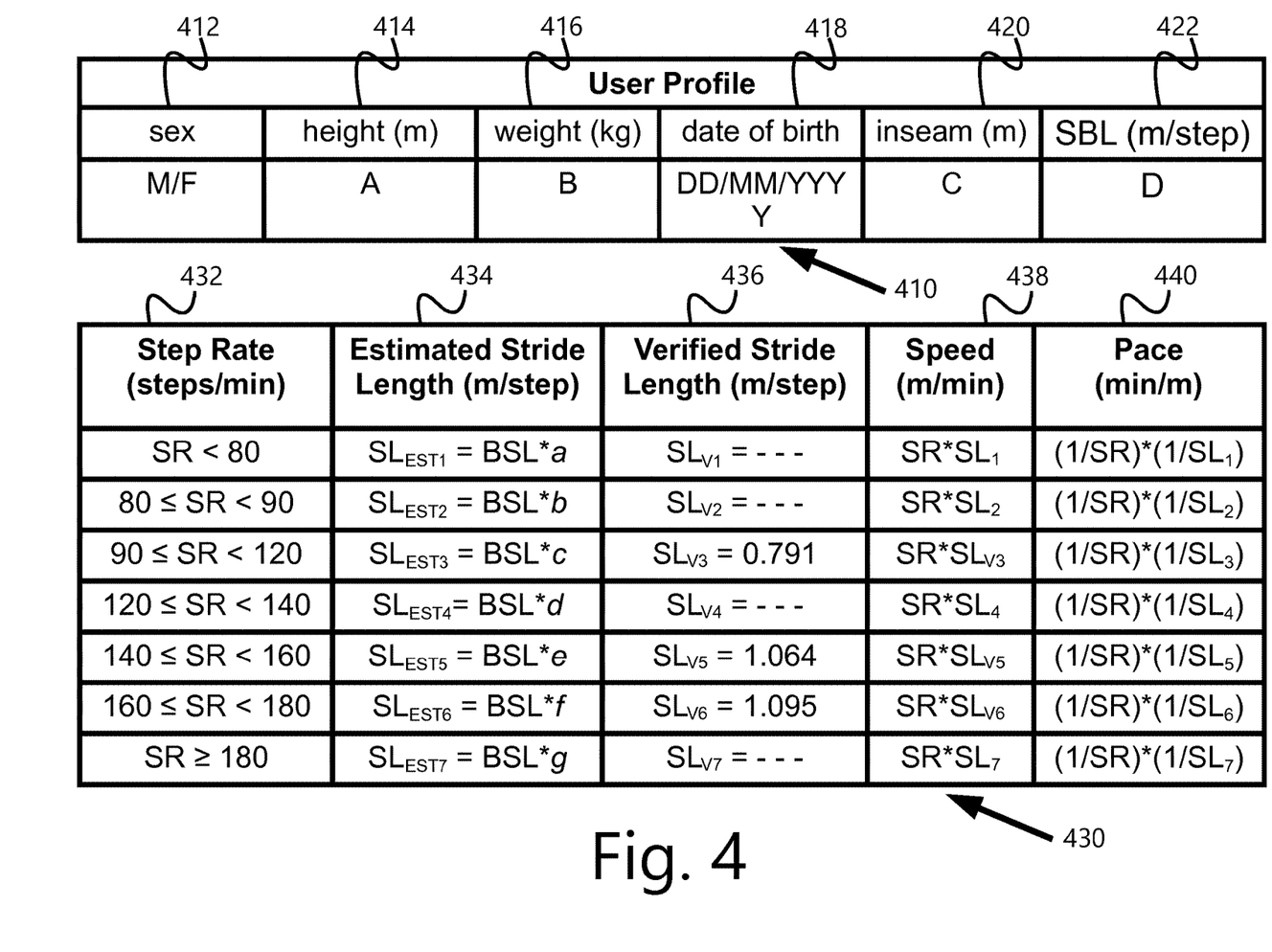
FIG. 4 depicts some aspects of an illustrative embodiment of a record contained in a database, as described herein.

FIG. 4 depicts an illustrative embodiment of data contained within a database such as database 340 shown in FIG. 3. In one aspect, the database may contain one or more tables 410, 430 comprising data (e.g., records in each row of one or more tables) associated with activity information, user-specific information, estimated stride length data, and/or historical or verified stride length data. In one embodiment, some of the data contained in the database may be compiled from past activity sessions during which collected, sensed, input, or analyzed data was received. Alternatively or additionally, some or all of the data may populated prior to use of apparatus 100 by the user in an activity based on one or more inputs by the user. In other embodiments, some or all of the data may be received or collected from a third party or secondary device that collected or otherwise possesses the data. In further embodiments, the data may be a combination of third party/secondary device data and data collected by apparatus 100 (either directly from the user or collected during an activity session).

In one aspect, table 410 may comprise user-specific information. In one embodiment, table 410 comprises sex information 412, height information 414, weight information 416, date of birth (or age) information 418, inseam information 420, and stride base length information ("SBL") 422. Other embodiments may include less, more, or alternative information pertaining to the user, including but not limited to, outseam information, fitness level information, preferred activity information, location information associated with where apparatus 100 is/will be worn or carried, and/or body type information. As shown in FIG. 4, the user specific information is received and/or recorded according to the metric system, but any suitable system or units may be used.

In another aspect, the user may input information for recording in table 410 via navigation of one or more menus of apparatus 100 and/or indicating values using any suitable input method (switches, buttons, touchscreens, etc.). In one embodiment, the user may input one or more of sex information 412, height information 414, weight information 416, date of birth information 418, and inseam information 420. In a further embodiment, some or all of this information can be used to determine and record SBL information 422. For example, in one embodiment, SBL may be determined based, at least in part, on one or more items of collected user-specific information. In one embodiment, SBL may be determined based on sex and height information, i.e., SBL=f (sex, height). In one example of such an embodiment, male users may be assigned some constant m, female users may be assigned some other constant f, and SBL may be determined by calculating the user's height multiplied by the sex-determined constant.

Obviously, this is only one relatively simple formulation for determining the user's SBL. In other embodiments, SBL may be determined based on some other algorithm or function that takes into account any one more of the user-specific information items.

In another aspect, apparatus 100 may be configured for use with multiple users. In such embodiments, database 340 may comprise multiple user profile tables 410, each corresponding to a respective user and containing information unique to that user. In operation, one such user may input identifying information to apparatus that may direct apparatus 100 to the appropriate user profile table 410 for an ongoing or future activity.

In a further aspect, table 430 may comprise stride length data associated with one or more users. In one embodiment, table 430 may comprise step rate information 432, estimated stride length information 434, verified stride length information 436, speed information 438, and pace information 440. In other embodiments, table 430 may comprise less, more, or alternative information. For example, table 430 may comprise other information, including but not limited to, calorie expenditure information, activity duration information, activity intensity information, and/or activity location information.

In one embodiment, during a monitored activity (e.g., walking, running, exercising, etc.), a user's step rate ("SR") may be determined based, at least in part, on the number of steps a user takes in a period of time, i.e., SR=f(steps, t). The SR information 432 may comprise a plurality of SRs or a plurality of SR ranges. For example, as depicted in FIG. 4, SR information 432 may comprise the following ranges of step rate recorded in steps per minute: SR<80; 80≤SR<90; 90≤SR<120; 120≤SR<140; 140≤SR<160; 160≤SR<180; and SR≥180. Of course, these ranges are only illustrative of the possibilities and any number of ranges and corresponding limits may be used. In some embodiments, rather than SR ranges, table 430 may comprise a row of data corresponding to each possible SR between zero and some upper limit.

In one aspect, estimated stride length information ("$SL_{EST}$") may be determined based, at least in part, on SR information 432 and the user's BSL information 422 from table 410, i.e., $SL_{EST}$=f(SR, BSL). In the embodiment depicted in FIG. 4, $SL_{EST}$ may be determined by multiplying a user's BSL by a constant associated with the determined SR or SR range of the user. Thus, when it is determined that the user's SR is less than, for example, 80 steps/min, BSL may be multiplied by a constant a. When it is determined that the user's SR is greater than or equal to 80 steps/min but less than 90 steps/min, $SL_{EST}$ may be determined by multiplying BSL by a constant b, and so on for each respective SR range. Obviously, this is only one possible method of determining an estimated stride length. Alternative methods may take into account fewer, more, or alternative items of information, including but not limited to, the type of activity in which the user is engaged, the user's height, weight, age, inseam, etc.

Generally, as a user's step rate increases, the user's stride length increases. Thus, the constants used for calculating $SL_{EST}$ may increase as the user's determined SR increases. In other words, in one embodiment, a<b<c<d<e<f<g. In one embodiment, a-g may each correspond to constants between zero and one. In other embodiments, a-g may correspond to constants between zero and one hundred. Any suitable values may be used and may depend, in part, on how BSL for a user is determined in table 410.

In another aspect, a user's speed (measured in distance/time) and pace (measured in time/distance) may be determined based, at least in part, on the user's SR and $SL_{EST}$. For example, a user's speed may be determined by multiplying the user's SR (steps/time) by the user's $SL_{EST}$ (distance), i.e., speed=SR*$SL_{EST}$. Pace is the inverse of speed, i.e., pace=time/distance or 1/speed. Thus, a user's pace may be determined by multiplying 1/SR by 1/$SL_{EST}$. As shown in FIG. 4, speed and pace are presented in meters per minute and minutes/meter, respectively, however, any suitable units of distance and time may be used for both or either determination.

In a further aspect, apparatus 100 may be configured to determine a verified stride length corresponding to a step rate or step rate range of the user. In one embodiment, and as described above, apparatus 100 may comprise a GPS module or some other components configured to detect the user's physical location and/or how far the user has traveled during an activity session. When such data is available, it may be used to determine a verified stride length of the user when exhibiting a particular step rate or step rate range. For example, if apparatus 100 determines that the user has taken some number of steps within a period of time and, in light of GPS or physical location data, has traveled some distance in the same time period, then not only can the user's step rate be determined, i.e., the number of steps taken divided by the time period, but the user's average stride length during the time period may also be determined, i.e., the distance traveled divided by the number of steps taken.

In other embodiments, the user may be able to set apparatus 100 to a calibration mode for determining the user's verified stride length to be associated with a step rate or step rate range. In such a calibration mode, for instance, apparatus 100 may prompt the user to walk, jog, or run for a predetermined or fixed period of time. Based, at least in part, on the distance traveled and number of steps taken by the user in that predetermined or fixed period of time, apparatus 100 can determine the user's step rate and associated, verified stride length. In another example of a calibration mode, apparatus 100 may prompt the user to take a predetermined or fixed number of steps/strides. Based, at least in part, on the distance traveled by the user and time elapsed in taking the predetermined or fixed number of steps/strides, apparatus 100 can similarly determine the user's step rate and associated, verified stride length. In a further example of a calibration mode, apparatus 100 may prompt the user to walk, jog, or run (i.e., traverse) a predetermined or fixed distance. Based, at least in part, on the number of steps taken by the user and the time elapsed in traversing the predetermined or fixed distance, apparatus 100 can determine the user's step rate and associated, verified stride length.

In still further embodiments, verified stride length information 436 may be determined and/or associated with respective step rates or step rate ranges even when a GPS signal is unavailable or apparatus 100 lacks a GPS module or some other component(s) configured to detect the user's physical location and/or how far the user has traveled during an activity session. For example, a treadmill, stair-stepper, or stationary bicycle may be used in conjunction with a calibration mode substantially similar to those discussed previously. In one embodiment, a user on a treadmill, for example, may be prompted to walk, jog, or run on the treadmill at a predetermined or fixed speed or pace for a predetermined or fixed period of time. Based, at least in part, on the number of steps taken by the user during the predetermined or fixed period of time, apparatus 100 can determine the user's step rate and associated, verified stride length. Alternatively, the user may be prompted to walk, job, or run on a treadmill, for example, at a predetermined or fixed speed or pace for a predetermined or fixed distance. Based, at least in part, on the number of steps taken by the user while traversing the predetermined or fixed distance, apparatus 100 can determine the user's step rate and associated, verified stride length.

Regardless of the method used to determine a verified stride length, the verified stride length may then be recorded in table 430 corresponding to the appropriate step rate or step rate range.

As discussed above, generally, a user's stride length increases as the user's step rate increases. Nonetheless, a user's stride length at one step rate may not be indicative of the user's stride length at another step rate. That notwithstanding, in further embodiments, where the estimated stride length of a user is shorter than the verified stride length for the user at a particular step rate or within a step rate range, it may be inferred that the estimated stride lengths for the user at other step rates or step rate ranges may also be shorter than the user's actual (or verified) stride length at those other step rates or step rate ranges. Similarly, where the estimated stride length of a user is longer than the verified stride length for the user at a particular step rate or within a step rate range, it may be inferred that the estimated stride lengths for the user at other step rates or step rate ranges may also be longer than the user's actual (or verified) stride length at those other step rates or step rate ranges. Thus, the estimated stride lengths of the user at step rates or step rate ranges different from that at which the verified stride length has been determined may be incrementally increased or decreased in light of a comparison of the verified stride length to the estimated stride length at the confirmed step rate or step rate range.

For example, as shown in table 430, GPS or other location information may be used to verify the user's stride length when the user exhibits a step rate between 90 and 120 steps/min. For the sake of illustration, assume that the verified stride length ($SL_{V3}$) of the user of 0.791 m/step was greater than the estimated stride length $SL_{EST3}$ of the user at the same step rate. It may then be inferred that the estimated stride lengths of the user at the remaining step rate ranges are similarly shorter than the actual, albeit unverified, stride lengths of the user at those step rates. Thus, the estimated stride lengths of the user at the remaining step rates may be incrementally increased in proportion to the difference between the estimated and verified stride lengths at the verified step rate range (i.e., a step rate between 90 and 120 steps/min).

Continuing with this illustration, GPS or other location information may then be used to verify the user's stride length when the user exhibits another step rate between 140 and 160 steps/min. Again, for the sake of illustration, assume that the verified stride length ($SL_{V5}$) of the user of 1.064 m/step was shorter than the estimated stride length $SL_{EST5}$ of the user at the same step rate. It may then be inferred that the estimated stride lengths of the user at the remaining step rate ranges where no verified stride length has been determined are similarly longer than the actual, albeit unverified, stride lengths of the user at those step rates. Thus, in this iteration, the estimated stride lengths of the user at the remaining unverified step rates may be incrementally decreased in proportion to the difference between the estimated and verified stride lengths at the newly verified step rate range (i.e., a step rate between 140 and 160 steps/min).

This iterative process, adjusting estimated stride lengths based, at least in part, on verified stride lengths of the user at other step rates or step rate ranges may continue until a verified stride length has been determined for the user at each step rate or step rate range.

In further embodiments, even verified stride length determinations may be further refined through the collection of similar data during later activity sessions. For instance, during a first activity session, the user may exhibit a first verified stride length at a particular step rate, but during a second, later activity session, the user may exhibit a second verified stride length at the same step rate. Numerous reasons for such a discrepancy exist, including but not limited to, the health of the user and the topography traversed during the activity session. In such instances, a moving average of the verified stride lengths during the two activity sessions may be used to update the verified stride length for the user at that step rate in table 430.

In one aspect, where apparatus 100 is used in a context in which GPS or location data either cannot be received or would not be helpful, the user's step rate in conjunction with either the user's estimated or verified stride length at that step rate may be used to determine the user's approximate speed and/or pace during the activity session. For example, where the user is in a location at which a GPS signal cannot be received or the user is in a gymnasium exercising on a stationary bicycle, treadmill, or stair-stepper machine, apparatus 100 may still approximate the user's speed and pace based, at least in part, on the information contained in table 430.

In one embodiment, where verified stride length information 436 is available for the user at a determined step rate or within a determined step rate range, then that verified stride length information may be used to determine the user's speed and pace without the assistance of GPS or other physical location information, i.e., speed=$SR*SL_V$ and pace=inv(speed). In further or alternative embodiments, where verified stride length information 436 has not been recorded for a determined step rate exhibited by the user, the user's speed and pace may still be approximated without the assistance of GPS or other physical location information based, at least in part, on the estimated stride length associated with the user's measured step rate, i.e., speed=$SR*SL_{EST}$ and pace=inv(speed).

It should be noted that although the above examples illustrate how a user's speed and/or pace may be determined even when GPS or other physical location information is unavailable, additional or alternative information may also be determined, including but not limited to, calorie expenditure information, total distance information, and activity intensity information. Moreover, although tables 410 and 430 are described as being contained in database 340 of apparatus 100, in other embodiments, tables 410 and 430 may be contained elsewhere in apparatus 100. Alternatively, tables 410 and 430, or any subset of data contained therein, may be stored in a database of another secondary or third party device. Further, some or all of the data in the tables may be collected by apparatus 100 or by the secondary or third party device.

Figure 5:
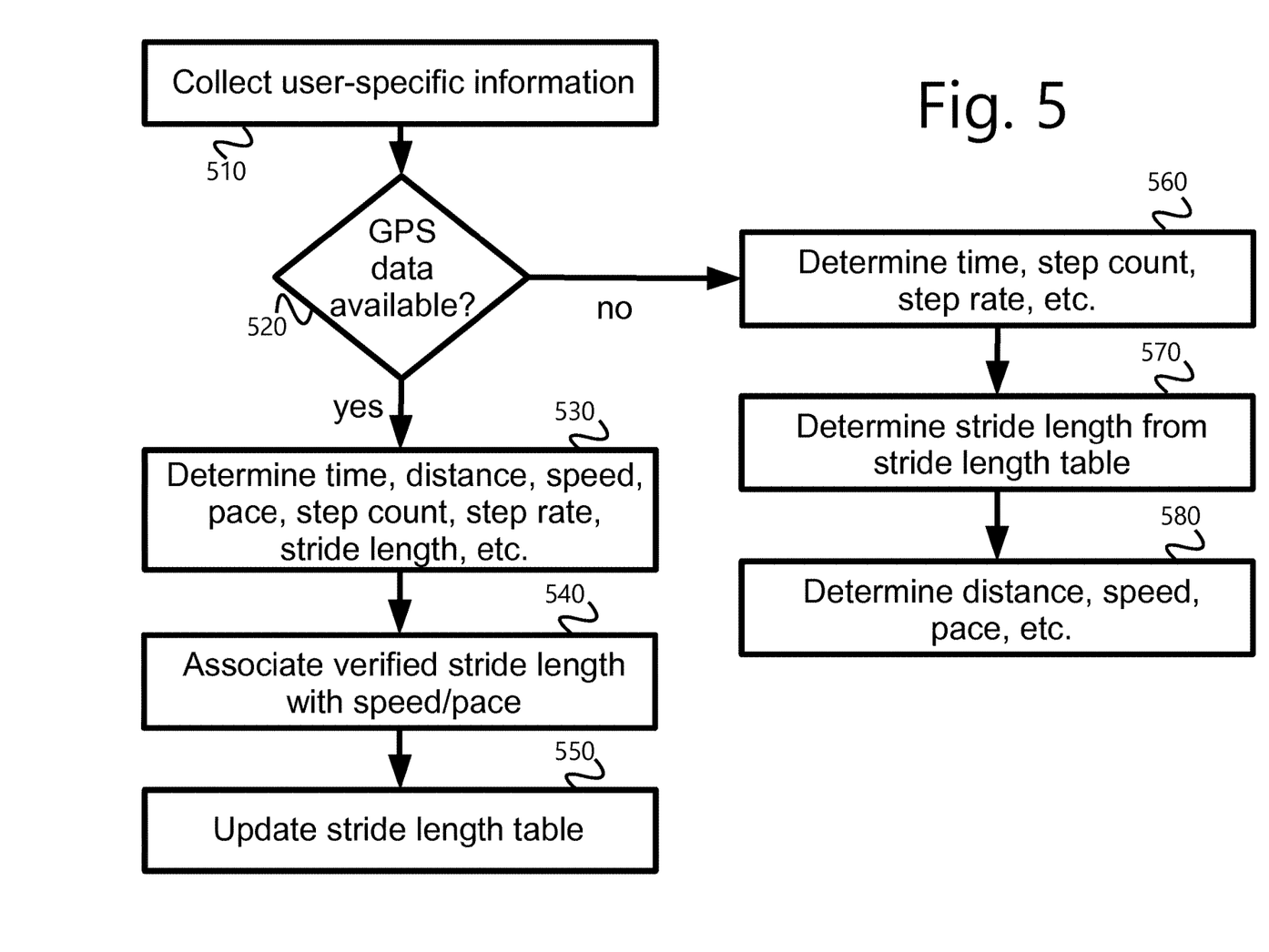
FIG. 5 depicts some aspects of an illustrative embodiment of a method as described herein.

FIG. 5 depicts an illustrative embodiment of a method for determining a user's stride length and providing distance, speed, pace, and other information to a user when a GPS signal or information may not be available.

In one aspect, at step 510, apparatus 100 may collect user-specific information from the user. Such user-specific information may include, but is not limited to, height, weight, age, sex, inseam, outseam, body type, and fitness level information. In other embodiments, less, more, or alternative information may be provided by the user such as one or more activities commonly engaged in, information representative of the user's environment, or any other suitable information specific to the user, the user's activities, and/or the user's environment.

In one embodiment, the user may input all or any portion of the user-specific information to apparatus 100 through the navigation of one or more menus displayed at apparatus and/or the manipulation of one or more switches, buttons, and displays of apparatus 100. Alternatively, apparatus 100 may collect some or all of the user-specific information from a third party or secondary device comprising the information. For example, user-specific information may be communicated to apparatus 100 by the user's smart phone, tablet, or personal computer.

One or more items of user-specific information may be stored at apparatus, for example at database 340, and/or used to populate one or more entries in a table similar to tables 410 or 430 of FIG. 4.

When the user is engaged in an activity and/or when apparatus 100 is monitoring the user's movements, at step 520, apparatus 100 may determine whether a GPS signal is available. The GPS signal, when available, may be used to locate the user and/or monitor the user's physical location during an activity or for the duration of a monitored period (which may be shorter or longer than the activity). In some cases, however, even when a GPS signal is available, GPS information may not be indicative of a user's activity. For example, apparatus 100 may receive a GPS signal when the user is exercising in a gym setting, jogging around a track, or running on a treadmill, stair-stepper, or stationary bicycle. A GPS signal may be available and the received GPS information may be accurate with respect to the user's physical location, but it does not accurately reflect the user's activity level or exertion. In one embodiment, the reliability of the GPS information received at apparatus 100 may be confirmed by comparing the GPS information to step counting information collected at apparatus 100. For example, during a monitored activity or during a predetermined period of time, apparatus 100 may determine that a user has taken a relatively high number of steps while GPS information indicates that the user's physical location has remained constant or changed very little. In such an instance, it may be inferred that the GPS information is not reliable even if a GPS signal is received without error. Alternatively, the user may input information to apparatus 100 indicating that GPS information will not be reliable for the user's ongoing or upcoming activity.

At step 530, when a GPS signal is available and/or the received GPS information appears reliable, that information may be used to one or more attributes associated with the user's activity. For example, a GPS signal or information may be used to monitor the physical distance traveled by a user during an activity or monitored period. In further embodiments, the GPS information in conjunction with step counting information determined at apparatus 100 may be used to determine or approximate the user's stride length during the activity or monitored period (i.e., stride length=distance traveled/number of steps taken). In still further embodiments, the GPS information and step counting information may be used in conjunction with time information to determine a user's step rate (or stride frequency), speed, or pace during the activity or monitored period. Of course, these activity attributes are only illustrative and other attributes may also be approximated, determined, or monitored, including but not limited to, calorie expenditure or activity intensity level.

As described above, generally, a user's stride length increases as the user's step rate or stride frequency increases. Thus, at step 540, the user's verified stride length (i.e., the confirmed stride length based on the number of steps taken and distance traveled by the user during the monitored period) may be associated with the determined step rate and/or a range of step rates (as described above with respect to FIG. 4).

At step 550, records stored at apparatus 100, such as in database 340, may be updated to include the verified stride length determination associated with the determined step rate of the user. In some embodiments, where verified stride length information has previously been stored and associated with the relevant step rate, more recently verified stride length information may replace older or previously-recorded verified stride length information. Alternatively, the earlier verified stride length information and the recently verified stride length information may both be used to calculate or approximate a new verified stride length to be associated with the relevant step rate or range of step rates. For example, an average or moving average of the current and any pre-existing verified stride lengths at the relevant step rate or range of step rates may be used to calculate a new verified stride length and/or update the records of apparatus 100. In other embodiments, the records containing the verified stride lengths of a user and/or the associations between those stride lengths and the user's step rate or ranges of step rate may be stored in a third party or secondary device apart from apparatus 100. Alternatively, apparatus 100 may temporarily store such records and associations, but that information may then be communicated from apparatus 100 to a third party or secondary device at a later time.

In a further aspect, verified stride length determinations associated with a step rate or range of step rates may also be used to update, alter, or refine estimated stride lengths associated with other step rates or ranges of step rates. For example, where the estimated stride length of a user is shorter than the verified stride length for the user at a particular step rate or range of step rates, it may be inferred that the estimated stride lengths for the user at other step rates or step rate ranges may also be shorter than the user's actual (or verified) stride length at those other step rates or step rate ranges. Similarly, where the estimated stride length of a user is longer than the verified stride length for the user at a particular step rate or range of step rates, it may be inferred that the estimated stride lengths for the user at other step rates or step rate ranges may also be longer than the user's actual (or verified) stride length at those other step rates or step rate ranges. Thus, in some embodiments, the estimated stride lengths of the user at step rates or step rate ranges different from that at which a verified stride length has been determined may be adjusted or updated (i.e., increased or decreased) in light of a comparison of the verified stride length to the estimated stride length at the respective step rate or step rate range.

In another aspect, where apparatus 100 determines that a GPS signal is unavailable or received GPS information is unreliable (as described above), apparatus 100 may still determine or approximate the user's stride length, distance traveled (whether actual distance or, in the case of activity performed on a treadmill, stair-stepper, or stationary bicycle, "virtual" distance), speed, pace, and other attributes associated with the user's activity.

At step 560, apparatus 100 may monitor and/or collect information pertaining to the number of steps a user takes during an activity or monitored period and, in conjunction with time, may further determine a step rate associated with the activity or monitored period.

At step 570, apparatus 100 may access a record, such as tables 410 or 430 in database 340, and determine or recall a stride length associated with the user's monitored step rate. For example, where a user's determined step rate is within a range of step rates of table 430, apparatus 100 may determine or recall a stride length associated with that range of step rates.

In one embodiment, apparatus 100 may determine or recall a verified stride length associated with the user's step rate. As described earlier, such a verified stride length may be based, at least in part, on GPS information received during previous/historical activities or monitoring periods. Alternatively, where no verified stride length has been associated with the user's determined step rate, apparatus 100 may determine or recall an estimated stride length associated with the user's step rate. Such an estimated stride length may be based, at least in part, on user-specific information such as the information contained in table 410 of FIG. 4.

Regardless of whether a verified stride length or estimated stride length is determine or recalled, apparatus may use this stride length to make further determinations regarding the user's activity. For example, and as previously described herein, one or more of time, a user's step count, a user's step rate, and stride length may be used to determine or approximate, for example, the user's distance traveled (actual or virtual), speed, pace, calorie expenditure, and workout/activity intensity. Thus, apparatus 100 may be configured to monitor, track, and collect a number of attributes associated with a user's activity even when no GPS signal may be received and/or when GPS information is unreliable or unhelpful.

While illustrative embodiments have been illustrated and described, it will be appreciated that various changes can be made therein without departing from the spirit and scope of the disclosure. Moreover, the various features of the embodiments described herein are not mutually exclusive. Rather any feature of any embodiment described herein may be incorporated into any other suitable embodiment.

Additional features may also be incorporated into the described systems, devices, and methods to improve their functionality. For example, those skilled in the art will recognize that the disclosure can be practiced with a variety of activity monitoring devices, including but not limited to activity, wellness, heart rate, blood pressure, exertion, and perspiration monitors, and that various components, sensors, and modules may be employed within such monitoring devices. The devices may or may not comprise one or more features to ensure they are water resistant or waterproof. Some embodiments of the devices may be hermetically sealed or even surgically implanted in the user's body. Alternatively, some embodiments of the devices may be embedded or integrated with clothing items such as shirts, shorts, pants, jackets, or shoes, to name only a few examples.

Other embodiments of the aforementioned systems, devices, and methods will be apparent to those skilled in the art from consideration of the specification and practice of this disclosure. It is intended that the specification and the aforementioned examples and embodiments be considered as illustrative only, with the true scope and spirit of the disclosure being indicated by the following claims.

What is claimed is:
1. An activity tracking apparatus, comprising:
one or more sensor modules comprising:
at least one accelerometer configured to detect acceleration information associated with movement of a user; and
an optical sensor module, an ambient light sensor module, or both;
a memory storing program instructions;
a database including one or more software and/or hardware components that cooperate to store, organize, sort, filter, and arrange data, wherein the database includes user profile information, historical activity and user-specific information, physiological parameter information, predetermined menu/display options, and other user preferences;
a status indicator that conveys information to the user; and
a processor for executing the program instructions, the processor configured to:
estimate a first stride length associated with a first step rate based, at least in part, on the user-specific information;
estimate a second stride length associated with a second step rate based, at least in part, on the user-specific information;
verify the first stride length for the first step rate based, at least in part, on the acceleration information from the at least one accelerometer; and
switch to a calibration mode where the activity tracking apparatus prompts a user to walk, jog, or run for a predetermined or fixed period of time or a fixed distance to calibrate the verified or adjusted stride length and wherein the calibration mode calibrates for a treadmill, stair-stepper, or stationary bicycle by prompting a user to use the treadmill, stair-stepper, or stationary bicycle to operate at a fixed speed or pace for a predetermined or fixed period of time;
apply one or more filters or pattern recognition to data received from the at least one accelerometer, wherein the one or more filters or pattern recognition is applied depending on where the activity tracking apparatus is worn or carried, the type of activity, or both;
adjust the second stride length for the second step rate based on the verified first stride length, wherein the second stride length is increased when the verified first stride length is greater than the estimated first stride length, and the second stride length is decreased when the verified first stride length is less than the estimated first stride length;

calculate a moving average of the verified first stride length over at least two activity sessions, where the at least two activity sessions are associated with the first step rate;

calculating a new verified stride length based upon the moving average of the verified first stride length;

based on determinations that current GPS data is available, the current GPS data is not reliable, and a current step rate of the user is within the first step rate, determine at least one of a distance travelled or rate of speed using the new verified first stride length; and based on determinations that the current GPS data is available, the current GPS data is not reliable, and the current step rate of the user is within the second step rate, determine the at least one of a distance travelled or rate of speed using the adjusted second stride length.

2. The activity tracking apparatus of claim 1, wherein verifying that the first stride length is performed in response to a determination that a GPS signal is available and reliable.

3. The activity tracking apparatus of claim 1, wherein a first constant is used to estimate the estimated first stride length, a second constant is used to estimate the estimated second stride length, the first step rate is less than the second step rate, and the first constant is less than the second constant.

4. The activity tracking apparatus of claim 1, wherein a first constant is used to estimate the estimated first stride length, a second constant is used to estimate the estimated second stride length, the first step rate is greater than the second step rate, and the first constant is greater than the second constant.

5. The activity tracking apparatus of claim 1, wherein the program instructions to adjust the second stride length based on the verified first stride length are further configured to:

adjust the second stride length based on the moving average of the verified first stride length, wherein the second stride length is increased when the moving average of the verified first stride length is greater than the first estimated stride length, and the second stride length is decreased when the moving average of the verified first stride length is less than the estimated stride length.

6. An activity tracking apparatus, comprising:
a memory storing program instructions;
a database on the memory, wherein the database comprises one or more tables comprising user-specific information, estimated stride length data, and/or historical or verified stride length data;
a processor for executing the program instructions to:
calculate estimated stride lengths based initially upon one or more user attributes;
store the estimated stride lengths in the one or more tables;
associate the estimated stride lengths with step rate ranges so that a plurality of step rate ranges populate the one or more tables, the step rate ranges being a range of steps with a similar stride length, wherein the estimated stride lengths are adjusted as one of the stride lengths is verified using GPS data;
switch to a calibration mode where the activity tracking apparatus prompts a user to walk, jog, or run for a predetermined or fixed period of time or a fixed distance to calibrate the verified or adjusted stride length and wherein the calibration mode calibrates for a treadmill, stair-stepper, or stationary bicycle by prompting a user to use the treadmill, stair-stepper, or stationary bicycle to operate at a fixed sped or pace for a predetermined or fixed period of time; and
an indicator that includes a plurality of light colors and each of the plurality of light colors are correlated to a heart rate or a pace within a numerical range and one of the plurality of light colors are illuminated when the heart rate or pace is detected within the numerical range;
based on a determination that current GPS data is available and is reliable, calculate at least one of distance travelled or rate of speed using the current GPS data; and
based on a determination that the current GPS data is not reliable, calculate the at least one of distance travelled or rate of speed using the verified or adjusted stride length that corresponds to a current step rate range;
wherein the table includes the user attributes and the user attributes are capable of being populated prior to use of the activity tracking apparatus.

7. The activity tracking apparatus of claim 6, wherein when one of the stride lengths is verified using the GPS data, another of the stride lengths is adjusted, and wherein the activity tracking apparatus is in communication with another device that comprises one or more accelerometers.

8. The activity tracking apparatus of claim 6, wherein when one of the stride lengths increases when verified using the GPS data, another of the estimated stride lengths also increases; and
wherein when one of the stride lengths decreases when verified using the GPS data, another of the estimated stride lengths also decreases.

9. The activity tracking apparatus of claim 6, wherein the one or more user attributes comprise one or more of gender information, height information, age information, weight information, health information, and inseam information, wherein the one or more user attributes are used to determine a stride base length, wherein each step rate range is associated with a constant, and wherein the stride base length is multiplied by the constants to set the initial stride lengths for the step rate ranges; and
wherein the constants increase as the step rate ranges increase.

10. The activity tracking apparatus of claim 6, wherein the initial stride lengths are directly proportionate to the associated step rate ranges, such that the initial stride lengths increase as the associated step rate ranges increase.

11. The activity tracking apparatus of claim 6, wherein the current GPS data is not reliable when a number of steps taken by the user is disproportionately high relative to a change in a physical location of the user.

12. The activity tracking apparatus of claim 6, wherein stride lengths are estimated for an unverified step rate range based upon the verified or adjusted stride length and the stride lengths are estimated based upon whether the step rate range of the verified or adjusted stride length is greater than or less than the unverified step rate range.

13. The activity tracking apparatus of claim 6, wherein the activity tracking apparatus includes a heart rate monitor and the plurality of light colors include a first color being correlated to a first heart rate numerical range, a second color being correlated to a second heart rate numerical range, and a third color being correlated to a third heart rate numerical range to convey information to a user regarding a status of a user's heart rate as measured by the heart rate monitor.

14. The activity tracking apparatus of claim 6, wherein the activity tracking apparatus includes one or more accelerometers and the one or more accelerometers include a three-axis accelerometer that is configured to convert movement or acceleration of a body into a digital measurement.

15. An activity tracking apparatus, comprising:
one or more sensor modules;
a memory storing program instructions;
a database including one or more software and/or hardware components that cooperate to store, organize, sort, filter, and arrange data, wherein the database includes user profile information, historical activity and user-specific information, physiological parameter information, predetermined menu/display options, and other user preferences; and
a processor for executing the program instructions to:
store stride lengths associated with step rate ranges, wherein the stride lengths are initially estimated based on the user-specific information so that an unverified stride length is generated and then the unverified stride lengths are adjusted as one of the stride lengths is verified using GPS data generating a verified or adjusted stride length;
determine whether recent or current GPS data is reliable based on a relationship between number of steps determined to be taken by the user and a change in a physical location of the user;
based on a determination that the recent or current GPS data is reliable, calculate at least one of distance travelled or rate of speed using the recent or current GPS data;
based on a determination that the recent or current GPS data is not reliable, calculate the at least one of distance travelled or rate of speed using the verified or adjusted stride length that corresponds to a current step rate range without assistance of the recent or current GPS data;
switch to a calibration mode where the activity tracking apparatus prompts a user to walk, jog, or run for a predetermined or fixed period of time or a fixed distance to calibrate the verified or adjusted stride length and wherein the calibration mode calibrates for a treadmill, stair-stepper, or stationary bicycle by prompting a user to use the treadmill, stair-stepper, or stationary bicycle to operate at a fixed speed or pace for a predetermined or fixed period of time;
applying one or more filters or pattern recognition methods to data received to determine a type of activity a user is engaged in; and
wherein the user-specific information comprise one or more of gender information, height information, age information, weight information, health information, and inseam information.

16. The activity tracking apparatus of claim 15, further comprising:
based on a determination that a GPS signal is not available, calculate the at least one of distance travelled or rate of speed using the stored stride length corresponding with the current step rate range.

17. The activity tracking apparatus of claim 15, wherein when one of the stride lengths is verified using the GPS data, another of the stride lengths is also adjusted.

18. The activity tracking apparatus of claim 15, wherein the stride lengths initially estimated are directly proportionate to the associated step rate ranges, such that the stride lengths initially estimated increase as the associated step rate ranges increase.

19. The activity tracking apparatus of claim 15, wherein the filters or pattern recognition methods are configured to filter or remove noise from the data that is attributable to accelerations unrelated to the user's steps.

20. The activity tracking apparatus of claim 15, wherein the activity tracking apparatus is a wrist watch or bracelet.

* * * * *